US008818515B2

(12) United States Patent
Bikson et al.

(10) Patent No.: US 8,818,515 B2
(45) Date of Patent: Aug. 26, 2014

(54) VOLTAGE LIMITED NEUROSTIMULATION

(75) Inventors: Marom Bikson, Brooklyn, NY (US);
Christoph Hahn, Hamburg (DE);
Shiraz A. Macuff, Hollis, NY (US);
Preet Minhas, Richmond Hill, NY (US);
Asif Rahman, Woodside, NY (US);
Justin Keith Rice, Brooklyn, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 13/350,343

(22) Filed: Jan. 13, 2012

(65) Prior Publication Data

US 2013/0184779 A1    Jul. 18, 2013

(51) Int. Cl.
*A61N 1/36* (2006.01)
*A61N 1/08* (2006.01)
*A61N 1/05* (2006.01)
*A61N 1/04* (2006.01)

(52) U.S. Cl.
CPC ............ *A61N 1/36025* (2013.01); *A61N 1/0526* (2013.01); *A61N 1/0456* (2013.01)
USPC ................................ 607/45; 607/63; 607/116

(58) Field of Classification Search
CPC ........ A61N 1/36; A61N 1/08; A61N 1/36025
USPC ....................... 607/45, 68, 116, 76, 69, 70, 71
See application file for complete search history.

(56) References Cited

U.S. PATENT DOCUMENTS

| 5,038,791 | A  | * | 8/1991 | Collins et al. | 600/509 |
|---|---|---|---|---|---|
| 7,317,948 | B1 | * | 1/2008 | King et al. | 607/62 |
| 7,571,007 | B2 | * | 8/2009 | Erickson et al. | 607/61 |
| 7,715,910 | B2 | * | 5/2010 | Hargrove et al. | 600/544 |
| 2005/0165458 | A1 | * | 7/2005 | Boveja et al. | 607/45 |
| 2006/0293720 | A1 | * | 12/2006 | DiLorenzo | 607/42 |
| 2007/0027486 | A1 | * | 2/2007 | Armstrong | 607/2 |
| 2007/0288064 | A1 | * | 12/2007 | Butson et al. | 607/45 |
| 2007/0293914 | A1 | * | 12/2007 | Woods et al. | 607/60 |
| 2008/0319505 | A1 | * | 12/2008 | Boyden et al. | 607/45 |
| 2009/0024187 | A1 | * | 1/2009 | Erickson et al. | 607/59 |

(Continued)

FOREIGN PATENT DOCUMENTS

| WO | WO2004075974 | * | 9/2004 | ........... A61N 1/0556 |
|---|---|---|---|---|
| WO | WO 2010/078441 A2 | * | 7/2010 | ............... A61N 1/36 |
| WO | WO 2010/120823 A2 | * | 10/2010 | ............... A61N 1/36 |
| WO | WO 2010/120824 A2 | * | 10/2010 | ............... A61N 1/36 |

*Primary Examiner* — Carl H Layno
*Assistant Examiner* — Erin Piateski
(74) *Attorney, Agent, or Firm* — Hoffmann & Baron, LLP

(57) ABSTRACT

Methods and systems for delivering voltage limited neurostimulation to a patient. In one aspect, a method includes initiating a flow of electrical current through a first electrode and a second electrode coupled to the patient and increasing the flow of electrical current toward a target value by increasing a voltage across the first electrode and second electrode. Prior to reaching the target value of electrical current, the method includes preventing the voltage across the first electrode and second electrode from increasing beyond a first predetermined limit; and subsequently, maintaining the voltage across the first electrode and second electrode at or within a predetermined range that does not exceed the first predetermined limit. The amplitude of the electrical current continues to increase toward the target value during at least part of a time when the voltage across the first electrode and the second electrode is maintained within the predetermined range.

20 Claims, 9 Drawing Sheets

(56) References Cited

U.S. PATENT DOCUMENTS

| | | | |
|---|---|---|---|
| 2009/0054950 A1* | 2/2009 | Stephens | 607/41 |
| 2010/0076254 A1* | 3/2010 | Jimenez et al. | 600/30 |
| 2010/0106207 A1* | 4/2010 | Dobak, III | 607/3 |
| 2010/0137929 A1* | 6/2010 | Libbey et al. | 607/5 |
| 2010/0262209 A1* | 10/2010 | King et al. | 607/62 |
| 2011/0060387 A1* | 3/2011 | King et al. | 607/62 |
| 2011/0066407 A1* | 3/2011 | Butson et al. | 703/2 |
| 2011/0160799 A1* | 6/2011 | Mishra et al. | 607/57 |
| 2011/0190847 A1* | 8/2011 | King et al. | 607/46 |

* cited by examiner

VOLTAGE LIMITED NEUROSTIMULATION

FIELD OF THE INVENTION

This specification relates to neurostimulation and, more particularly, to a voltage limited form of neurostimulation, such as transcranial direct current stimulation ("tDCS") to a patient.

BACKGROUND

Neurostimulation involves modulating the nervous system and electrically activating neurons in the body.

Transcranial direct current stimulation (tDCS) is a form of neurostimulation that uses constant, low current delivered directly to particular areas of the brain using electrodes. tDCS can be used, for example, as therapy for certain psychological disorders, such as anxiety disorders and depression.

SUMMARY

This specification describes technologies relating to voltage limited neurostimulation.

In general, one innovative aspect of the subject matter described in this specification can be embodied in methods that include the actions of initiating a flow of electrical current through a first electrode and a second electrode coupled to the patient and increasing the flow of electrical current toward a target value by increasing a voltage across the first electrode and second electrode. Prior to reaching the target value of electrical current, the method includes preventing the voltage across the first electrode and second electrode from increasing beyond a first predetermined limit; and subsequently, maintaining the voltage across the first electrode and second electrode at or within a predetermined range that does not exceed the first predetermined limit. The amplitude of the electrical current continues to increase toward the target value during at least part of a time when the voltage across the first electrode and the second electrode is maintained within the predetermined range.

These and other embodiments can each optionally include one or more of the following features.

For example, the method can include adjusting the voltage across the first electrode and the second electrode after the target current has been reached to substantially maintain the electrical current at the target value. Additionally, adjusting the voltage across the first electrode and the second electrode can include reducing the voltage across the first and second electrode as a resistance of from the first electrode to the second electrode reduces. Moreover, the method can further include substantially maintaining the electrical current at the target value for a period of time sufficient to produce a therapeutic effect in the patient. In some instances, the target value of current is between about 1 milliamp and about 3 milliamps and the period of time that the electrical current is substantially maintained at the target value is between about 10 minutes and 30 minutes. In some instances, the method includes delivering between about 600 millicoulombs and about 2400 millicoulombs of electric charge to the patient during the period of time that the electrical current is substantially maintained at the target value.

In certain embodiments, the method includes monitoring the flow of current and in response a determination that the monitored flow of current has not reached the target value within a predetermined amount of time (e.g., the time that may have previously been expected to be required), extending a period of time that the flow of current is to be delivered to the patient.

In some implementations, the method includes monitoring the flow of current, and taking a responsive action to a determination that the monitored flow of current has not reached the target value within a predetermined amount of time. Typically, the responsive action is selected from the group consisting of alerting a human operator (e.g., with an audible, visual or tactile alarm) and extinguishing the flow of electrical current.

According to some embodiments, a ramp-up period exists between a time that the flow of electrical current is initiated and a time that the voltage across the first electrode and the second electrode is prevented from increasing beyond the first predetermined limit. The ramp-up period can be between about 1 second and about 30 seconds. In some instances, the ramp-up period is about 10 seconds. In some implementations, the flow of electrical current increases during the ramp-up period at an average rate of no more than about 1.5 milliamps per 30 seconds.

The neurostimulation method can be, for example, transcranial direct current stimulation, transcranial alternating current stimulation or any other type of neurostimulation.

In certain implementations, the method includes monitoring the voltage across the first electrode and the second electrode; and disconnecting the voltage across the first electrode and the second electrode if the voltage across the first electrode and the second electrode exceeds a second predetermined limit indicating a circuitry malfunction. The predetermined second value typically is above the predetermined first value.

The predetermined range can be, for example, within about 10% of the first predetermined limit. In some embodiments, increasing the flow of electrical current toward a target value includes increasing the flow of electrical current monotonically. The voltage across the first and second electrodes can be a direct current voltage or an alternating current voltage.

Some embodiments of the method include applying a test stimulation to the patient, monitoring a test voltage and/or a test current associated with the test stimulation, generating a circuit model based on the monitored test voltage and/or test current, using the circuit model to set one or more parameters associated with the electrical current and/or voltage in the delivery of neurostimulation to the patient. Moreover, in some embodiments, the method includes adjusting one or more stimulation parameters associated with the delivery of neurostimulation to the patient in real-time.

According to certain implementations, the method includes increasing the voltage to a voltage level in a manner that accelerates a decrease in resistance across the electrodes.

In another aspect, a system for delivering neurostimulation to a patient includes a source of electrical current with a pair of output terminals. The source of electrical current is operable to initiate a flow of electrical current through the pair of output terminals and increase the electrical current toward the target value by increasing a voltage across the pair of output terminals. Prior to reaching the target value of electrical current, the system prevents the voltage across the pair of output terminals from increasing beyond a first predetermined limit and subsequently, maintains the voltage across the pair of output terminals at or within a predetermined range below the predetermined limit. The amplitude of the electrical current continues to increase toward the target value for at least part of a time when the voltage across the pair of output terminals is maintained within the predetermined range.

In some implementations, the system includes a target current setting device (e.g., a knob or the like) configured for manipulation by a human operator to set a target value for current to be delivered by the source of electrical current. In certain implementations, the system of claim 20 further includes a pair of electrically conductive cables coupled to the pair of output terminals, respectively, each cable having an electrode at a distal end thereof for coupling to the patient.

According to some embodiments, the system has a stimulation duration setting device (e.g., a knob or the like) configured for manipulation by the human operator to set a duration that the source of electrical current will deliver the target current. The source of electrical current is further configured to adjust the voltage across the pair of output terminals after the target current has been reached to maintain the electrical current substantially at the target value for the set duration. In some embodiments, adjusting the voltage across the pair of output terminals further includes reducing the voltage across the pair of output terminals to maintain the electrical current substantially at the target value for the set duration as a resistance from a first one of the output terminals to a second one of the output terminals becomes smaller.

Certain embodiments of the system include a timing indicator (e.g., a visual display) configured for indicating to the human operator, while the target value of current is being maintained, an amount of time remaining that the target value of current will continue to be maintained based on the set duration. The stimulation duration setting device, in some implementations, facilitates setting a duration that, if the target value of electrical current is delivered to the patient for a period of time that corresponds to the set duration, a therapeutic effect in the patient will be produced. In certain embodiments, the source of current is configured to deliver a target value of current between about 1 milliamp and about 3 milliamps, and wherein the stimulation duration setting device is configured to enable the human operator to set the duration to a value between about 10 minutes and 30 minutes.

In certain implementations, the target current setting device and the stimulation duration setting device are configured to enable the human operator to set the source of current to deliver between about 600 millicoulombs and about 2400 millicoulombs of electric charge to the patient during the period of time that the electrical current is substantially maintained at the target value.

Some embodiments of the system include a voltage limit setting device (e.g., a knob or the like) that may be configured for manipulation by the human operator to set the first predetermined limit.

In some implementations, the system includes an indication device (e.g., a visual display with a gage) for indicating to the human operator that the voltage across the pair of output terminals has reached and is being maintained at the first predetermined limit.

The source of current can, in some instances, be configured to ramp-up an amplitude of the electrical current between initiating electrical current flow and when the voltage across the output terminals is prevented from increasing beyond the first predetermined limit, wherein the ramp-up occurs over a period of time between about 1 second and about 30 seconds. In some instances, the flow of electrical current increases during ramp-up at an average rate of no more than about 1.5 milliamps per 30 seconds.

The neurostimulation can be, for example, transcranial direct current stimulation, transcranial alternating current stimulation or any other kind of neurostimulation.

In certain embodiments, the system includes a safety shut-down circuit (e.g., a breaker-based, fuse-based, or relay-based system, or the like). The safety shut-down circuit is configured to monitor the voltage across the output terminals and disconnect the voltage across the output terminals if the voltage across the output terminals exceeds a second predetermined limit indicating a circuitry malfunction. The predetermined second value is above the predetermined first value.

The voltage across the first and second electrodes can be, for example, alternating current voltage or direct current voltage.

Particular embodiments of the subject matter described in this specification can be implemented so as to realize one or more of the following advantages.

For example, safe and effective neurostimulation (e.g., transcranial direct current stimulation) can be provided. In a typical implementation, safety is provided by preventing the voltage across a pair of electrodes from exceeding some predetermined limit, which is relatively low and not typically considered dangerous. The techniques tend to have minimal effect on a patient's level of inconvenience and may reduce the patient's discomfort during the procedure, because the ramping of current tends to be slower than may otherwise occur.

In some implementations, the total voltage required by the device, both on the output and in internal components, is reduced increasing safety. The power and energy consumption of the device is reduced. The stimulation is more individualized and adaptive.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

The present application relates to systems and methods for delivering neurostimulation, such as transcranial direct current stimulation ("tDCS") or transcranial alternating current stimulation ("tACS") to a patient.

In general, tDCS uses a relatively constant, low flow of direct electrical current delivered directly to the brain area of a patient using small electrodes. More particularly, when the electrodes are placed in the regions of interest, electrical current flow through the electrodes induces intracerebral current flow. This intracerebral current flow can either increase or decrease neuronal excitability in specific areas being stimulated based on which type of stimulation is being used. This change of neuronal excitability leads to alteration of brain function, which can be used in various therapies as well as to provide more information about the functioning of the human brain. For example, tDCS can be used as therapy for certain physiological disorders, such as anxiety disorders and depression, as well as a tool for motor rehabilitation in stroke patients. tDCS is completely noninvasive and, therefore, easy to administer, safe and convenient for patients or recipients of tDCS.

Figure 1:
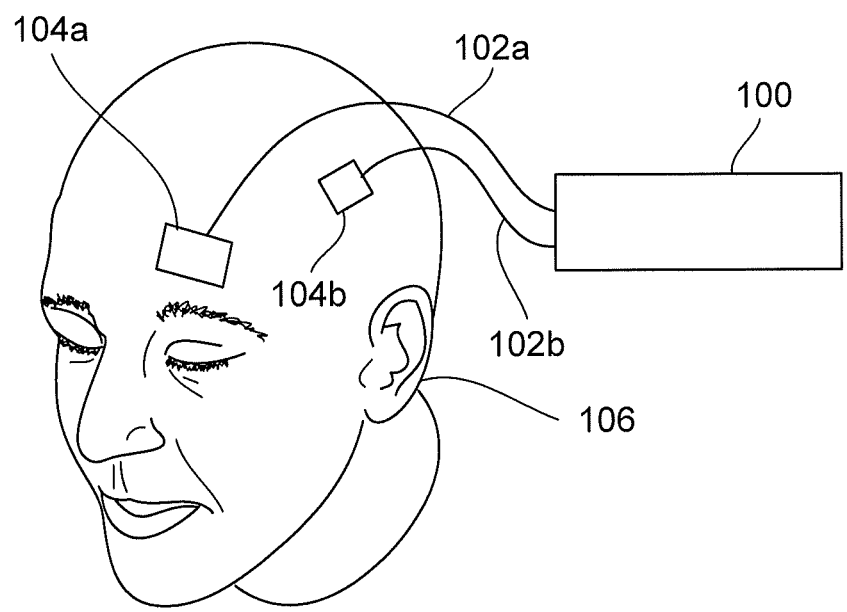
FIG. 1 is a perspective view of a transcranial direct current stimulation device coupled to a patient.

FIG. 1 shows an exemplary tDCS device 100 connected via a pair of electrical cables 102a, 102b with electrodes 104a, 104b at their respective distal ends to the head of a human patient 106. In the illustrated example, a first one of the electrodes 104a is positioned near a front portion of the patient's head and a second one of the electrodes 104b is positioned back on the top of the patient's head, displaced at least several centimeters away from the first electrode 104a. Of course, effective tDCS can be achieved with a variety of different electrode configurations.

In a typical implementation, before the tDCS is initiated, a human operator would program into the tDCS device 100 at least: 1) a target value of current, and 2) a duration for delivering the target value of current to the human patient 106.

In response to a prompt from the human operator, the tDCS device 100 initiates a flow of electrical current through the first electrode 104a, through the patient and through the second electrode 104b. The tDCS increases the flow of electrical current toward the target value by increasing a voltage across the first electrode 104a and second electrode 104b. However, prior to reaching the target value of electrical current, the tDCS prevents the voltage across the first electrode 104a and the second electrode 104b from increasing beyond a first predetermined limit and subsequently, maintains the voltage across the first electrode 104a and second electrode 104b within a range that may include the first predetermined limit, but that does not exceed that limit.

While the voltage is maintained across the first electrode 104a and the second electrode 104b, the amplitude of the electrical current being delivered to the patient continues to increase toward the target value for at least part of the time that the voltage is so maintained. This is believed to be due, at least in part, to the fact that the electrical resistance from the first electrode 104a and the second electrode 104b through the patient tends to decrease at least during the initial phases of tDCS current delivery. Therefore, since the voltage is maintained—or substantially maintained within a range close to the predetermined limit—and the resistance decreases, the flow of electrical current continues to increase. In a typical implementation, the system is operable such that the flow of electrical current increases until it either reaches or becomes very close to the target value. This occurs, therefore, without the voltage exceeding the predetermined limit.

In general, preventing the voltage across the first electrode 104a and 104b from increasing beyond the predetermined limit and maintaining the voltage at or near the predetermined limit prior to reaching the target value of electrical current causes the tDCS device 100 to take longer than it otherwise would take to begin delivering current at or substantially at the target value. However, the predetermined limit typically is set such that the difference in time is between about 10 to 60 seconds, which has very little impact on the effectiveness of the tDCS and the patient's convenience. In some instances, the difference in time may be between about 10 and 30 seconds.

By preventing the voltage from exceeding a predetermined voltage—that is typically well below a voltage that could give rise to concern about safety—the chances of potentially dangerous spikes in electrical current occurring are low. Therefore, in a typical implementation, this technique provides a high safe way to deliver tDCS. Moreover, the increase in time required for the current to reach its target value when the voltage is being capped before the target value is reached does not significantly increase the time of a typical tDCS procedure, which may last overall for about ten to fifteen minutes or longer, does not substantially increase the level of inconvenience for the patient. Additionally, since the flow of electrical current is increased in a fairly gradually manner, the degree of discomfort for the patient receiving tDCS may be reduced. Finally, the difference in time to reach the target current does not present a noticeable impact on the therapeutic impact of the overall tDCS procedure.

Figure 2A:
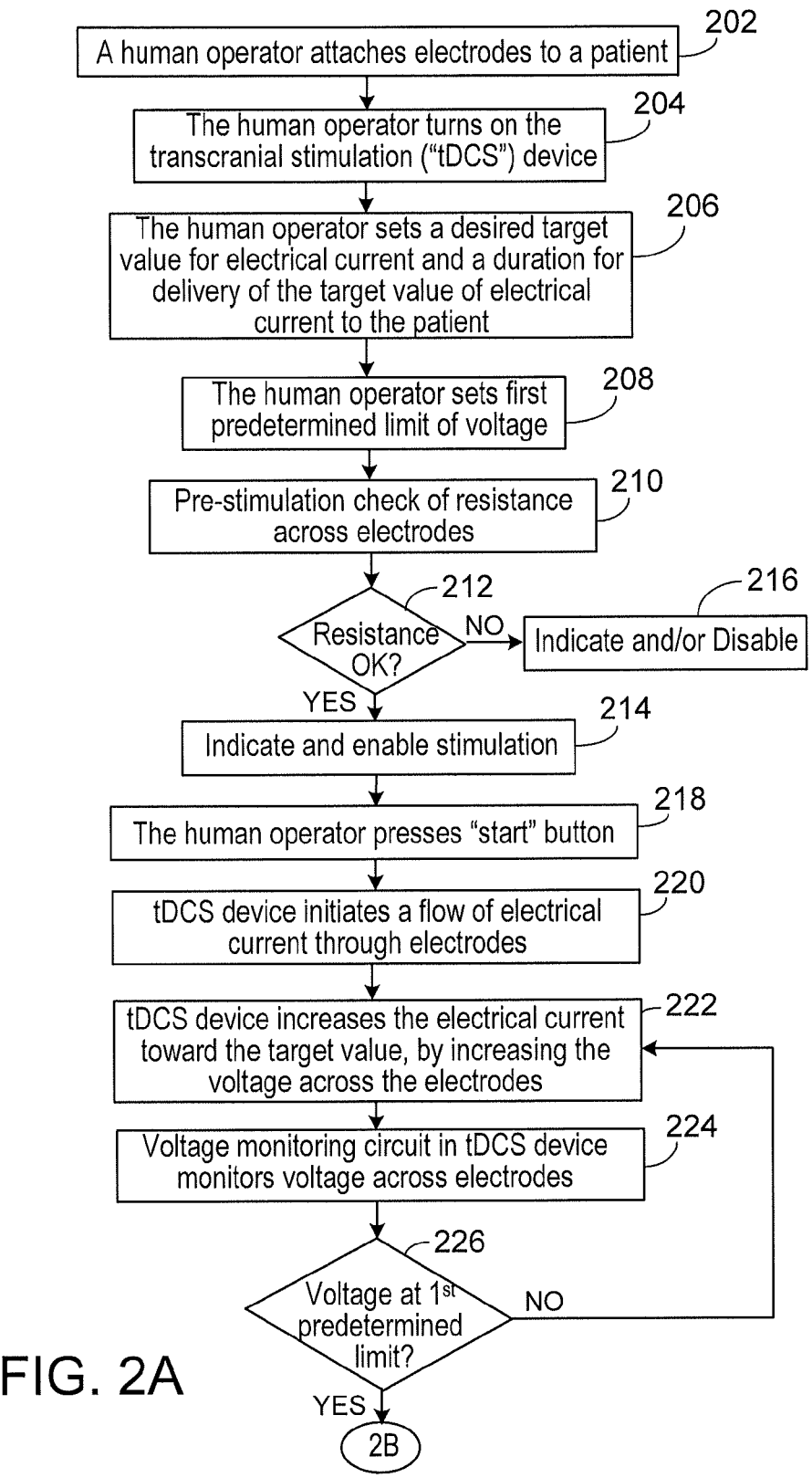
FIGS. 2A and 2B are a flowchart showing an exemplary method of delivering transcranial direct current stimulation.
Figure 2B:
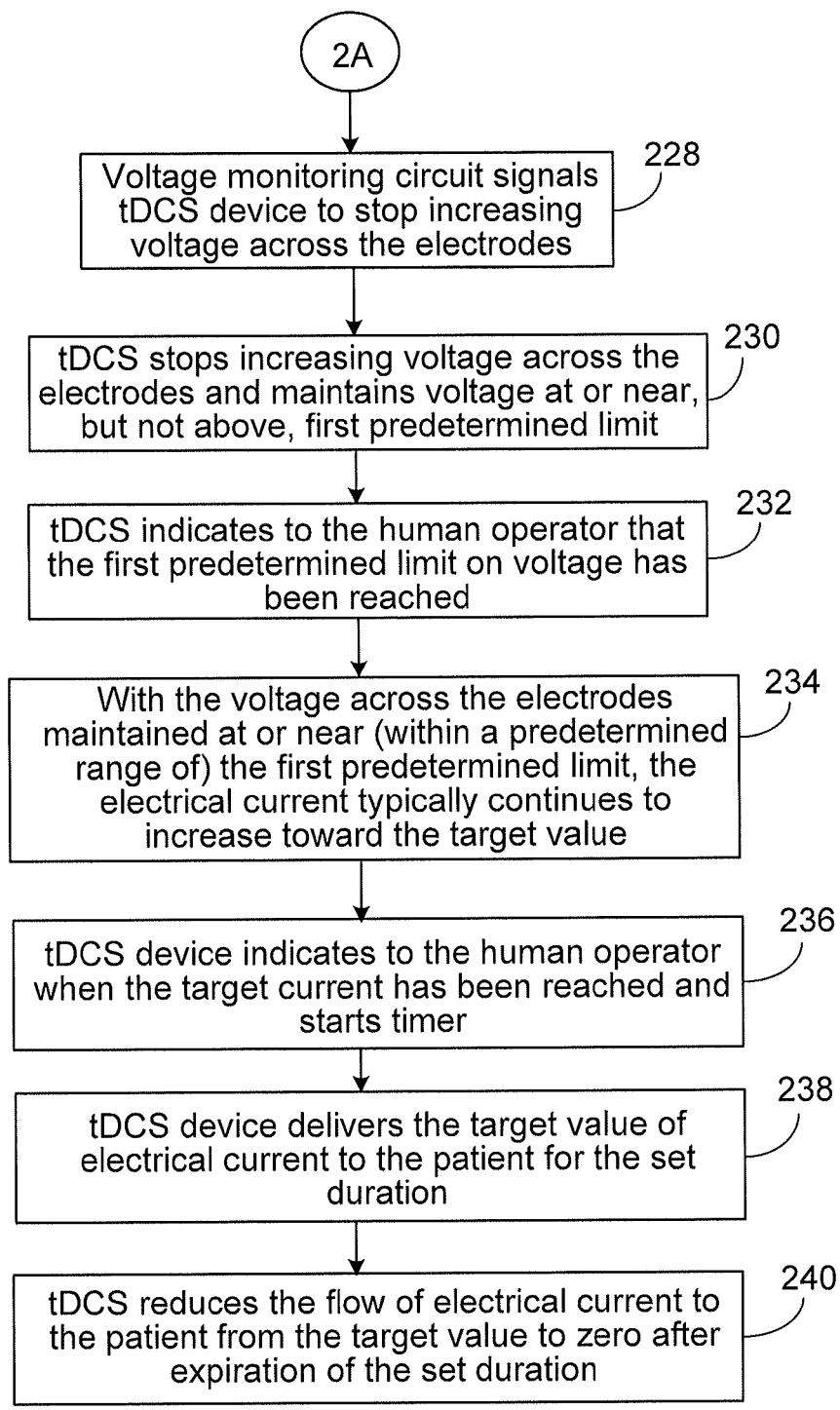

FIGS. 2A and 2B show a detailed example of a tDCS procedure implementing the techniques discussed above.

According to the illustrated method, a human operator attaches (at 202) electrodes (e.g., electrodes 104a, 104b) to a patient (e.g., patient 106). Typical electrodes used in tDCS include a sponge material coupled to a conductive rubber member. For the tDCS procedure, the sponge material is usually soaked in a conductive fluid, such as an electrolytic fluid or the like. The electrodes can be attached to the patient in a wide variety of ways including, for example, by using an adhesive material, or by virtue of the electrodes being incorporated into a hat that the patient wears. When attaching the electrodes, it is important to ensure a strong connection between the skin and the electrode. In a typical implementation, this can be facilitated by, for example, cleaning the area of skin to which the electrodes are to be coupled. Also, careful positioning of electrodes can be important to the successful delivery of therapeutic tDCS.

Electrodes can come in various sizes and different benefits can generally be achieved by using each of the different sizes. In general, a smaller sized electrode can help achieve a more focused stimulation of a site while a larger electrode can help ensure that a larger region of interest is being stimulated. If an electrode is placed incorrectly, a different site or more sites than intended may be stimulated resulting in faulty results.

Typically, one electrode is placed over the region of interest and the other electrode, the reference electrode, is placed in another location in order to complete the circuit. This reference electrode may be placed on the head (as shown in FIG. 1) or on another area of the body, such as the neck or shoulder on an opposite side of the body from the region of interest.

Once the electrodes have been connected to the patient, the human operator then turns the tDCS device "on" (at 204).

Next, the human operator (at 206) sets a desired target value for electrical current to be delivered to the patient and duration for delivery of the target value of electrical current. These parameters can be set to a variety of different values. In some implementations, for example, the target value of current may be set to a value between about 1 milliamp and about 3 milliamps (e.g., about 1.5 milliamps) and duration for delivery of the target value of electrical current may be set to between about 10 minutes and about 30 minutes (e.g., about 10 minutes). These values may be modified, of course, but, typically, the target value of current and duration are set so as to produce a desired result (e.g., a therapeutic result) in the patient.

The combination of desired target value for current and duration deliver a particular amount of electrical charge to the patient. In some instances, the desired target value for current and the duration are such that an electrical charge between about 600 millicoulombs and about 2400 millicoulombs will be delivered to the patient during the period of time that the electrical current is substantially maintained at the target value.

In a typical implementation, the set target value for current is one that the tDCS device will deliver in a substantially steady manner over a duration that corresponds to the set duration. This duration setting typically does not include ramp up and/or ramp down times for electrical current.

Referring again to the illustrated method, the human operator sets the first predetermined voltage limit (at 208). The first predetermined voltage limit is a voltage level that the voltage of the tDCS device will not exceed during normal tDCS operation, assuming all device components are operating properly. In this regard, the first predetermined voltage limit acts as a limit for available operating voltage. This is particularly significant, for example, during the current ramp-up period when the voltage across the tDCS electrodes is being increased to cause the electrical current to increase toward the target value. Once the voltage across the tDCS electrodes reaches the first predetermined limit, the tDCS device prevents the voltage from increasing any further and maintains the voltage either at or near, but not above, the first predetermined limit.

The first predetermined voltage limit is not a trip voltage (i.e., the tDCS device continues operating when the first predetermined voltage is reached or exceeded). Indeed, the voltage produced by the tDCS device can and, in fact, often does reach the first predetermined limit during normal operation of the tDCS device. In some implementations, the tDCS may include a high voltage trip set to a voltage (i.e., a "second predetermined voltage limit") that is higher—in some instances, significantly higher—than the first predetermined voltage limit. The second (higher) predetermined voltage limit typically is intended to shut the tDCS device off upon the occurrence of a potentially dangerously high voltage level. The second predetermined voltage limit may be adjustable by a human operator, but more typically it would be factory set and, unlike the first predetermined limit, not be adjustable by human operators in the field.

In a typical implementation, the tDCS device includes an adjustment knob, keypad, or the like for setting the various operational parameters (e.g., the first predetermined voltage, the duration, etc.).

Next, in the illustrated method, the tDCS device conducts a pre-stimulation check of the electrode resistance (at 210).

This check typically involves measuring the electrical resistance from electrode to electrode (or from one output terminal on the tDCS to the other output terminal). In most instances, this measure of electrical resistance provides an indication of the quality of contact between the electrodes and the patient's skin. It is important that this done before the main procedure gets under way, therefore, because poor contact can lead, in some instances, to a great deal of discomfort in the patient.

The resistance measurement may be accomplished in a number of ways. For example, a known (or measured) voltage may be applied across the electrodes and the resulting current is measured. The resulting current is an indirect indicator of the resistance between the electrodes since the resulting current is inversely proportional to that resistance. Alternatively, a known (or measured) current may be passed through the electrodes and the resulting voltage drop across the electrodes measured. The resulting voltage drop is an indirect indicator of the resistance between the electrodes since the resulting voltage drop is directly proportional to the resistance between the electrodes. In general, a high resistance between the electrodes is indicative of a poor quality connection and a low resistance between the electrodes is indicative of a good quality connection.

According to the illustrated method, if the tDCS determines (at 212) that the contact resistance is acceptable, then the tDCS (at 214) indicates this result to the human operator, for example, with an audible, visual or tactile indication, and enables the human operator to begin a stimulation procedure. If, on the other hand, the tDCS determines (at 212) that the contact resistance is not acceptable, then the tDCS (at 216) indicates the unacceptable contact quality to the human operator. According to the illustrated implementation, the tDCS enters a "disabled" operating mode, whereby the human operator is prevented from beginning a stimulation procedure until some corrective action is taken.

If the connections are poor, there are a number of corrective measures that the human operator may take. These measures include, for example, pressing down on the electrodes, adding electrolyte to the electrodes, cleaning the interface between the electrodes and the person's skin, replacing the electrodes, replacing the cables, etc.

In some implementations, the tDCS device merely provides an indication of contact resistance to the human operator with a visual, audible or tactile indicator and the decision to proceed directly to the stimulation procedure, take some corrective action first or abort the procedure is left up to the human operator. In general, there is no single "best" reading for all applications; however, generally a higher quality reading indicates "better" electrode-skin contact. In these instances, however, it is the responsibility of the human operator to ensure that the contact quality reading is appropriate for a given application prior to stimulation. If corrective measures are implemented, in a typical implementation, a visual, audible or tactile indicator on the tDCS device, such as a contact quality meter, can operate to provide continual (or at least somewhat regular) updates to the human operator about the contact resistance so that the human operator can properly gage the effectiveness of whatever corrective measures are being taken.

Once an acceptable contact quality has been established, according to the illustrated method, the human operator (at 218) presses the start button on the tDCS to begin the neurostimualtion procedure.

In response to the human operator pressing the start button, the tDCS device (at 220) initiates a flow of electrical current through the electrodes to the patient. In a typical implementation, this is done by applying a voltage across the electrodes. The flow of electrical current through the electrodes is influenced, at least in part, by the resistance of the circuit outside of the electrodes (i.e., the portion of the circuit that extends from one electrode, through the patient and back to the other electrode. Typically, during the initial moments of electrical current flow, the electrical resistance of this external circuit changes from a relatively high value to a significantly lower value.

The tDCS device (at 222) increases the flow of electrical current toward the target value that was set by the human operator (see 206). The tDCS typically does this by increasing the voltage across the electrodes (and across the tDCS output terminals that the electrodes are connected to). The period of time that the voltage is being increased to produce an increased current flow may be referred to as a ramp-up period. In a typical implementation, current flow increases in a substantially monotonic manner, that is, without decreasing at all. However, in some instances, there may be moments during the ramp-up period when the voltage and/or current flow decreases or dips, at least momentarily. However, during the ramp-up period, the general trend of both voltage and current flow is to increase, with the current increasing toward the target value.

Also during the ramp-up period, the electrical resistance of the external circuit (i.e., the electrical resistance from electrode to electrode, through the patient) continues to drop, typically, in a substantially asymptotic manner. It is believed that the flow of current through the external circuit helps cause the drop in resistance over time.

Typically, the first predetermined voltage limit is set to a value that is low enough that, under expected operating conditions, the tDCS device will produce a voltage that reaches the first predetermined limit before the flow of current reaches the target value. Moreover, the first predetermined voltage limit is set to a value that is high enough that, if the electrode voltage is subsequently maintained at the first predetermined voltage level, then the target current will be reached within a certain time frame after the electrode voltage reaches the first predetermined voltage limit. In a typical implementation, this time period is between about 10 second and about 60 seconds (e.g., between about 30 seconds and about 50 seconds).

Therefore, during system operation, the tDCS device can be expected to (and will) stop increasing the voltage across the electrodes before the target value is reached. Thus, in a typical implementation, the tDCS prevents the voltage across the electrodes from increasing beyond the first predetermined limit that was set by the human operator (see 208) and, subsequently, maintains the voltage across the electrodes at or within a range that does not exceed the first predetermined limit.

In the illustrated implementation, a voltage monitoring circuit in the tDCS monitors (at 224) the voltage across the electrodes. In a typical implementation, the voltage monitoring circuit monitors the voltage the entire time that voltage is being produced across the electrodes or output terminals of the tDCS device.

According to the illustrated implementation, as long as the actual voltage across the electrodes has not reached the first predetermined limit (as determined at 226), then the tDCS continues to increase the electrical current flow through the electrodes (at 222). However, if the tDCS device determines (at 226) that the actual voltage across the electrodes has reached the first predetermined limit that was set by the human operator (see 208), then the voltage monitoring circuit signals the tDCS device (at 228) to stop increasing the voltage across the electrodes. The determination of whether the voltage across the electrodes has reached the first predetermined limit typically is made based on a signal generated by the voltage monitoring circuit.

The tDCS stops increasing the voltage across the electrodes (at 230) and subsequently maintains the voltage across the electrodes at or near, but not above, the first predetermined voltage limit. According to the illustrated implementation, the tDCS device (at 232) indicates to the human operator that the first predetermined limit on voltage has been reached. This indication can be visual, audible or tactile.

Typically, after ceasing to increase the voltage, the tDCS device maintains the voltage across the electrodes substantially at the first predetermined voltage limit, at least until the target current is reached. During this time, the flow of current continues to increase (234) toward the target value—even though the voltage is being maintained substantially constant—due, at least in part, to the electrical resistance in the external circuit continuing to change in a downward manner. However, the rate at which the flow of current actually increases is less than the rate otherwise would be if the tDCS device were producing a voltage above the first predetermined voltage limit.

According to the illustrated method, when the target current has been reached the tDCS (at 236) starts a timer and indicates to the human operator, with a visual, audible or tactile indicator, that the target current has been reached.

The tDCS device (at 238) delivers the target current to the patient for the duration that was set by the human operator (see 206). During this period of time, the resistance may continue to drop. As such, the tDCS device may decrease the voltage across the electrodes in view of the decreasing resistance to substantially maintain the electrode current at or at least very near the target current. However, typically during this period of time, the resistance does not change much.

After the target current has been applied for the set duration, the tDCS device (at 240) reduces the flow of electrical current to the patient from the target value back to zero.

Figure 3:
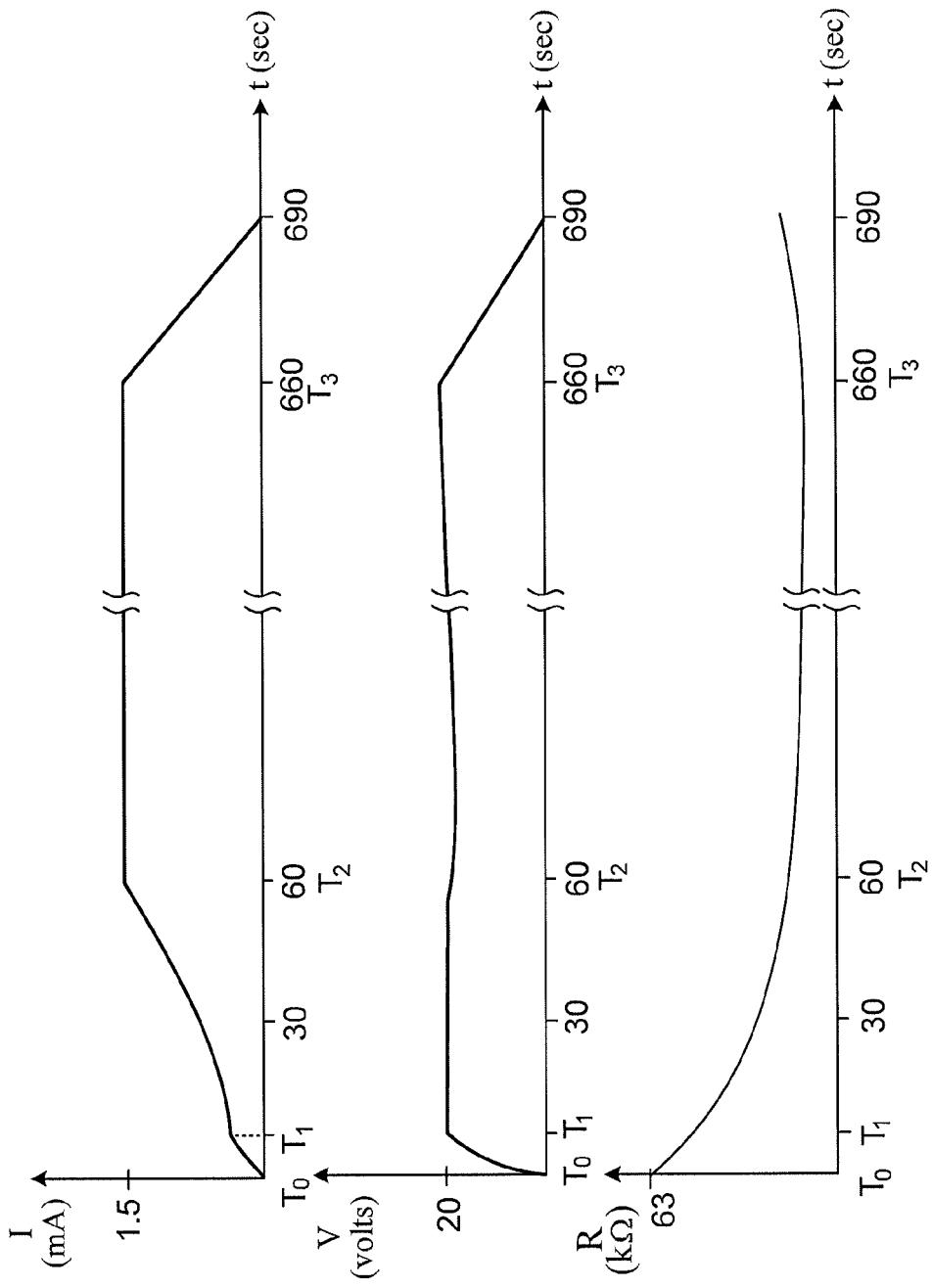
FIG. 3 includes three graphs showing how current, voltage and resistance, respectively, changes over time during an exemplary transcranial direct current stimulation procedure.

FIG. 3 shows the changes in electrical current flow ("I" in the top chart), voltage ("V" in the middle chart) and resistance ("R" in the bottom chart) that occur over time during an exemplary tDCS procedure. In the illustrated charts, the electrical current flow, the voltage, and the resistance are represented by the vertical axes. Time ("t" in each chart) is represented by the horizontal axes in the charts. In the illustrated example, the target current has been set at 1.5 milliamps, the first predetermined limit on voltage has been set at 20 volts and the duration has been set at 10 minutes (i.e., 600 seconds).

As shown, at time T0, the process is initiated. The voltage (V) across the electrodes beings to ramp-up from zero volts and the current also begins to ramp-up toward the target value of 1.5 milliamps. In the illustrated example, the initial external resistance is 63 kilo-ohms, which begins to drop essentially as soon as the electrical current begins to flow.

At time T1, the voltage (V) being produced by the tDCS device across the electrodes reaches the first predetermined voltage limit of 20 volts. Notably, this occurs before the current (I) reaches the target value of 1.5 milliamps.

Beginning at time T1, the tDCS device prevents the voltage across the electrodes from increasing beyond the first predetermined limit of 20 volts. Subsequently, the tDCS device maintains the voltage (V) across the electrodes at the predetermined voltage limit of 20 volts until time T2, which is 60 seconds in the illustrated example, when the current (I) reaches the target value of 1.5 milliamps. Between T1 and T2, the external resistance continues to drop and, therefore, the current continues to increase even though the voltage is maintained at a substantially constant level.

According to the illustrated implementation, the target current of 1.5 mA is substantially maintained for the set duration of 10 minutes (i.e., 600 seconds) from time T2 until time T3. During this period of time, from T2 to T3, the external electrical resistance continues to decrease in a substantially asymptotic manner. In order to maintain the flow of electrical current substantially constant, at or about the target value of 1.5 milliamps, the voltage is reduced in a manner that is proportionally tracks the changes in external electrical resistance during this time period.

After time T3, the voltage and current are ramped down to zero over a period of time, which, in the illustrated implementation, is about 30 seconds. The external electrical resistance during this period of time tends to increase a bit, as represented in the illustrated example.

Figure 4:
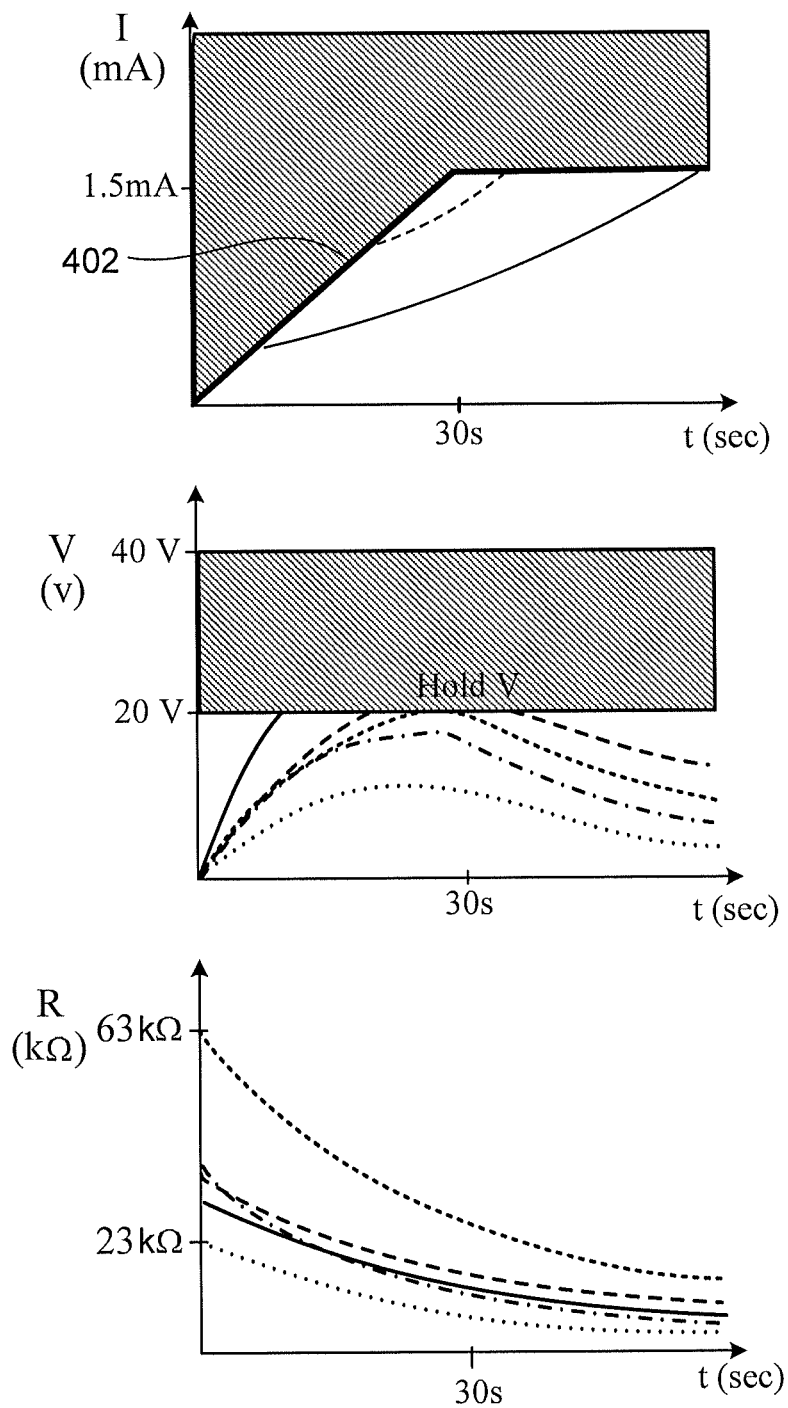
FIG. 4 includes three graphs showing an example of how current, voltage and resistance, respectively, changes over time during part of an alternative exemplary transcranial direct current stimulation procedure.

FIG. 4 shows the changes in electrical current flow ("I" in the top chart), voltage ("V" in the middle chart) and resistance ("R" in the bottom chart) that occur over time during five different scenarios during the first minute or so of exemplary tDCS procedures. In the illustrated charts, the electrical current flow, the voltage, and the resistance are represented by the vertical axes and time is represented by the horizontal axes. Each scenario corresponds to a different starting value for resistance. The matching curves in each chart show how the current, voltage and resistance change over time given the corresponding starting resistance.

In the illustrated example, the target current has been set at 1.5 milliamps and the first predetermined limit on voltage has been set at 20 volts.

The current chart (i.e., the top chart in FIG. 4) has a line 402 that extends up from 0 milliamps at 0 seconds at a constant slope of 1.5 milliamps per 30 seconds to the 30 second mark and then extends diagonally across the chart. This line 402 defines a limit, beyond which, at least in certain instances, may cause the patient to experience discomfort. In none of the scenarios shown does the current ever exceed the limit represented by this line 402. The line 402 is somewhat arbitrary and may be modified in different situations.

In each of the scenarios represented, the voltage (V) across the electrodes ramp-up from zero volts and the current also begins to ramp-up toward the target value of 1.5 milliamps. Also, the external resistance begins to drop-off from its initial value essentially as soon as the electrical current begins to flow. Shortly thereafter, the voltage (V) across the electrodes reaches the first predetermined voltage limit of 20 volts. Notably, in each scenario, this occurs before the current (I) reaches the target value of 1.5 milliamps.

In each scenario, once the voltage (V) across the electrodes reaches the first predetermined voltage limit of 20 volts, the tDCS device prevents the voltage (V) across the electrodes from increasing beyond the first predetermined limit. Subsequently, the tDCS device maintains the voltage (V) across the electrodes at or near, but not below, the predetermined voltage limit at least until the current (I) reaches the target value of 1.5 milliamps. In each scenario, the external resistance decreases substantially asymptotically across the chart.

Notably, in each scenario, the amplitude of the electrical current continues to increase toward the target value when the voltage across the first electrode and the second electrode is maintained at or near, but not above, the predetermined first limit on voltage.

The appropriate voltage limit can be adjusted based on one or a combination of factors including the electrode material used including any electrolyte composition, electrode size, electrode position on the body, time since last stimulation, skin preparation, stimulation waveform including target amplitude in current and duration, condition of the subject, other known hazards, presence of injury, subject age, subject body mass index, measurements before or during stimulation including resistance or impedance monitoring, or subject gender. For example: tDCS was administered for six minutes (30 s ramp-up, 5 min stimulation, 30 s ramp-down) to healthy adult subjects, using a designed battery-run circuit which allows free adjustment of maximum output voltage and current magnitude. Rubber electrodes were wrapped in saline soaked sponge pads (35 cm2, Soterix Medical Inc. Easy-PAD). Electrode montage C3-SO. Initially, sponge pads were moistened with 15 ml of 0.9% concentrated saline. The impedance across electrodes was measured one minute before and after stimulation by injecting three currents (I=50 µA, 100 µA, 150-200 µA) and recording the required potential. Stimulation was not started unless the initial impedance was ≤50 kΩ (I=50 µA). In order to decrease impedance, the necessary amount of saline was added to the sponge pads and soft pressure was applied to ensure uniform contact and wetting of the hair and scalp. Care was taken to minimize excessive wetting and dripping across the scalp. At least a 24 hour interval in between stimulation. Current was ramped up and down linearly over 30 seconds. Rubber electrodes wrapped in saline soaked sponges were held in place over the primary motor cortex and superior to contralateral orbit by rubber elastic straps or tDCS head-gear. Stimulation was conducted with current magnitudes of 0.5 mA (with a predetermined voltage limit of 10 volts) and 1 mA (with a predetermined voltage limit of 12 volts); 1.5 mA (with a predetermined voltage limit of 14.5 volts); 1.5 mA (with a predetermined voltage limit of 14.5 volts) and 2.0 mA (with a predetermined voltage limit of 17 volts); and 2.5 mA (with a predetermined voltage limit of 17 volts); 2.7 mA (with a predetermined voltage limit of 17 volts) and 2.8 mA (with a predetermined voltage limit of 17.5 volts); 3.0 mA (with a predetermined voltage limit of 20 volts); 4.0 mA (with a predetermined voltage limit of 25 volts). In another example: Subject are male or female adults—aged 28-55 years Subjects were interviewed and examined by a neurologist and found to be free of psychiatric or neurological disorders or potentially confounding medications tDCS was delivered through a battery-driven constant current stimulator connected to a HD-tDCS adaptor device (Soterix Medical Inc.—SMI, New York, N.Y.). Sintered Ag—AgCl electrodes were attached to High-Definition plastic holders (SMI) filled with conductive gel, embedded in an electroencephalogram (EEG) cap and attached to the adaptor device. High-Definition electrodes were arranged on the skull according to a "4×1-ring" configuration with the central electrode placed over the APB hotspot. The return electrodes were spaced 5 cm radially around the active electrode at the corners of a square. The polarity was defined by the active electrode, both anodal and cathodal stimulation was used. The current was delivered with a ramp-up time of 10 s, held at 1 mA for 20 min, and then ramped down over 10 s. Stimulation was conducted with current magnitudes of 0.5 mA (with a predetermined voltage limit of 15 volts) and 1 mA (with a predetermined voltage limit of 20 volts); 1.5 mA (with a predetermined voltage limit of 20 volts); 1.5 mA (with a predetermined voltage limit of 20 volts) and 2.0 mA (with a predetermined voltage limit of 20 volts); and 2.5 mA (with a predetermined voltage limit of 25 volts); 2.7 mA (with a predetermined voltage limit of 25 volts) and 3.0 mA (with a predetermined voltage limit of 255 volts); 3.5 mA (with a predetermined voltage limit of 30 volts); 4.0 mA (with a predetermined voltage limit of 30 volts).

Figure 5:
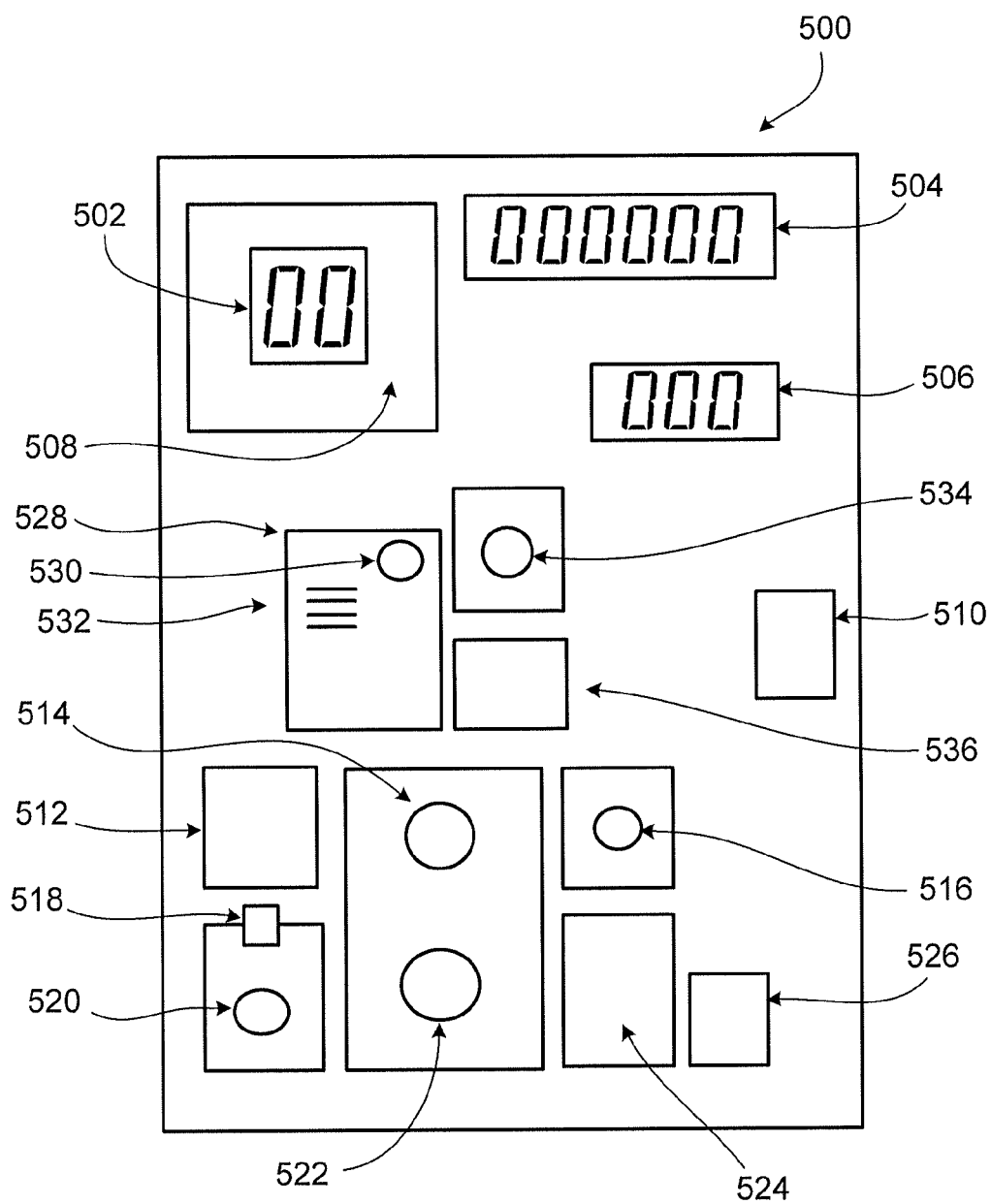
FIG. 5 is a front view of an exemplary transcranial direct current stimulation device.

FIG. 5 shows a control panel 500 for an exemplary tDCS device that is adapted to implement one or more of the techniques disclosed herein.

The illustrated tDCS device 500 has a three light emitting diode (LED)-based displays 502, 504 and 506.

Display 502 is adapted to indicate the amount of time remaining in an ongoing stimulation procedure. Display 504 is adapted to indicate the actual amount of current being produced by the tDCS device. Display 504 also may provide information on device functions including the device state, stage of stimulation, or voltage limiting activity. Display 504 may prompt for actions that should be taken by operator or provide information about the history of stimulation.

Display 506 is adapted to indicate the resistance of the external circuit and/or the voltage being applied across the electrodes or across the tDCS device's output terminals.

A light 508 is provided next to the time display 502. In some implementations, the tDCS device is operable such that if the actual current being produced by the tDCS device does not reach the target value fast enough (e.g., due to high electrical contact resistance or other reason), then the tDCS device may extend the duration of the procedure beyond what the human operator set as the duration to ensure that an appropriate amount of charge is delivered to the patient during the procedure. If this happens, then the light 508 can illuminate to alert the human operator that the duration has been extended.

An adjustable slider 510 is provided that the human operator can manipulate to set the first predetermined voltage limit. In some implementations, an override can be provided to allow the tDCS device to operate without the first predetermined voltage limit.

A pre-stimulation check button 512 is provided that can be manipulated by the human operator to initiate a pre-stimulation system check (e.g., to check the external circuit resistance and, perhaps other system parameters) to help facilitate proper system operation. After the check has been completed, information may be provided to the user and/or component functionality in the tDCS device may be enabled or disabled.

A duration adjustment knob 514 is provided that can be manipulated by the human operator to adjust the duration of the stimulation (e.g., to 5, 10, 15, or 20 minutes). This is usually set prior to the start of stimulation.

A SHAM switch 516 is provided to activate or deactivate SHAM. In general, when SHAM is activated, the tDCS device emits a brief current but then remains off for the remainder of the stimulation time. With sham stimulation, the person receiving the tDCS does not know that they are not receiving prolonged stimulation; this provides a control condition for experiments, which can be double-blinded.

The panel has a low battery indicating light 518 that illuminates to indicate a low battery condition. The panel has a power switch 520 that turns the tDCS device on or off. A target current knob 522 enables the human operator to adjust the target value for current to a desired setting. This is generally set prior to the start of stimulation. A start button 524 enables the human operator to start the stimulation. A stop button 526 enables the human operator to stop the stimulation.

A light 530 provides a visual indication of when the actual voltage across the electrodes is at the predetermined first limit. Either the intensity of the light and or frequency of flashing provide indication of this condition. For example, a flashing light may indicate that the condition exists during the first 30 seconds, whereas a steady light may indicate that the condition exists after 30 seconds of stimulation.

An audible speaker 532 provides information on activities related to limiting the voltage at the predetermined first limit. For example, the speaker may beep when the voltage across the electrodes has reached the predetermined first limit.

An activation switch 534 is provided to enable or de-activate the voltage limiting functionality associated with the first predetermined voltage limit.

An array of lights 536 is provided to give the human operator some indication as to the quality of the electrode connections. For example, in a typical implementation, the indicated quality of the electrode connection may increase as the selected lit light on the array moves from left to right, such that the right most light, for example, indicates an optimal electrode quality. The electrode quality may relate to the voltage required to provide a specific current, such that the electrode quality decreases as the required voltage increases. The light array may be calibrated such that for a given target current when the electrode connection is good enough such that the first voltage limit will not be reached, the lit light on the array is on the right side of the array. As the voltage approaches the first voltage limit, the lit lights move to the left until a light corresponding to the first voltage limit is reached. This light may be the leftmost light. If it is not the leftmost light, then even as the electrode quality contact deceases the light does not move further to the left because the voltage does not exceed the first voltage limit. The array may be labeled to indicate with light on the array corresponding to the first voltage limit. In some instances, the control unit on the device may help ensure that this is correct for the given set target current including that the first voltage limit may be a function of the target current.

Figure 6:
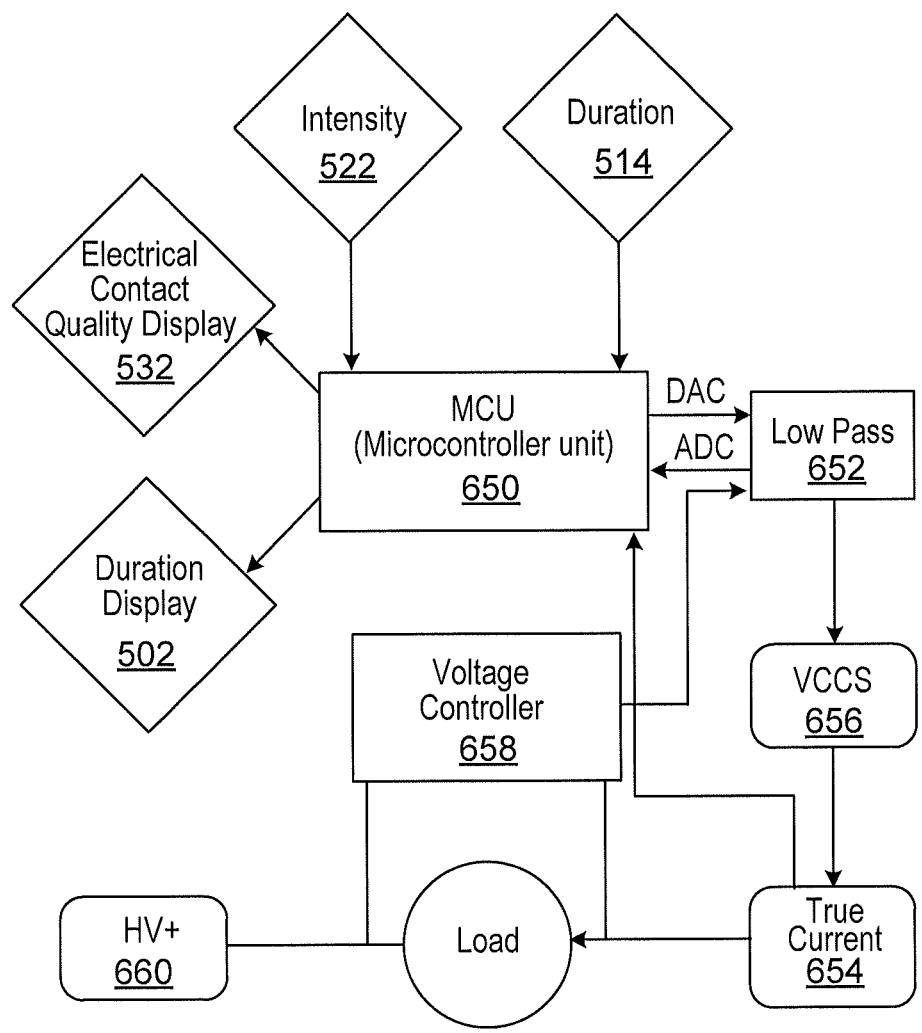
FIG. 6 is a partial schematic diagram of a transcranial direct current stimulation device.

FIG. 6 is a schematic block diagram of portions of a tDCS device similar to the tDCS device 500 in FIG. 5.

The illustrated tDCS device includes a microcontroller unit (MCU) 650, which is a data processing apparatus. The MCU 650 is coupled to the intensity adjustment devices 522 (e.g., a target current setting device) and the duration setting device 514. The MCU 650 also is coupled to the electrical contact quality display 532 and the duration display 502. The MCU 650 is also coupled to a low pass filter 652 and to a true current monitor 654. The low pass filter 652 is coupled to a voltage-controlled current source 656 and to a voltage controller 658. The voltage controller is connected across the load (e.g., the electrodes and the patient). HV+ 660 is a high voltage source that may be needed, in some instances, to achieve a particular current depending on the load resistance.

In a typical implementation, the signal coming from the micro controller 650 to the low pass filter 652 is a pulse width modulated signal which is converted to an analog signal by the low pass filter 652. This signal may be used to control the current. The voltage controlled current source 656 receives a voltage signal from the low pass filter 652 and converts this signal to a current.

The true current 654 represents an independent current meter that displays the current passing through the load. In the event of fault conditions, this provides the clinician with dosage being delivered. True current is in series with the current passing through the load.

Figure 7:
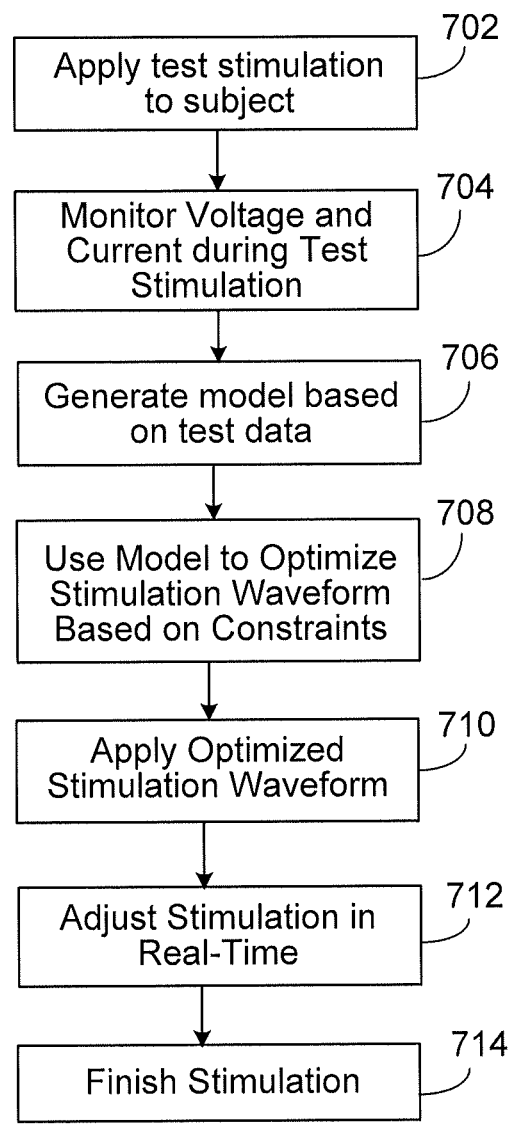
FIG. 7 is a flowchart of a modeling technique being used in conjunction with a stimulation procedure such as delivering transcranial direct current stimulation.

In certain embodiments, the techniques disclosed herein may be enhanced with the use of modeling, an example of which is represented in FIG. 7.

The illustrated method includes applying 702 a test stimulation to the subject (e.g., the patient). In a particular implementation, a protocol of current application is applied one or more times to one or more subjects. The current and voltage relationship is monitored during this period. The waveform applied and manner of control can be similar to the desired therapeutic waveform, or may be selected to be distinct in some or all aspect but still provide relevant model information. The test stimulation can be, for example, an on-off ramp, an impulse, or square wave.

The illustrated method further includes monitoring 704 voltage and current during the test stimulation. The information may be recorded in a variety of ways including, for example, by using an onboard data storage unit or telemetry to remote device. The application of test stimulation may involve repeated stimulation on the same subject, though preferably not on the same location and with a break in time, as well as measurements across subjects all of which is compiled into a single database.

The illustrated method includes generating 706 a model based on the test data.

The data is used to generate a model or parameterize a set of equations. The model may be based on lumped parameter circuit including any combination of R, L, and/or C components arranged in parallel or series circuits, with each component having a value parameterized. The circuit may further include non-linear elements including diodes and arbitrarily defined components. The model may be based on a differential equation of first, second, third, fourth, or fifth order, or higher orders. The model parameters may be constrained to match the data using a range of fitting tools including least-squares.

One model may be generated to fit all the data, or models specific to certain waveforms may be generated. For example, there may be a distinct model for each target current. In the preferred embodiment, a single model is used.

The illustrated method includes using 708 the model to optimize a stimulation waveform based on constraints.

The model is used to determine an optimal waveform for stimulation based on the model parameters generated and the desired stimulation performance constraints which may include any aspect of the stimulation waveform such as target current, limits on voltage, changing limited on voltage, or limited in rate of current change. The illustrated method also includes applying 710 an optimized stimulation waveform.

The stimulation is applied as optimized by the model. During stimulation current and voltage may be monitored and may be recorded.

The illustrated method includes adjusting 712 stimulation in real-time.

In some embodiments, based on the model and the real time monitoring to voltage and/or current, the stimulation may be further optimized.

The illustrated method includes finishing 714 the stimulation procedure. In some implementations, at the end of stimulation, the total current and voltage information may be recorded and used to further optimize the model.

Figure 8:
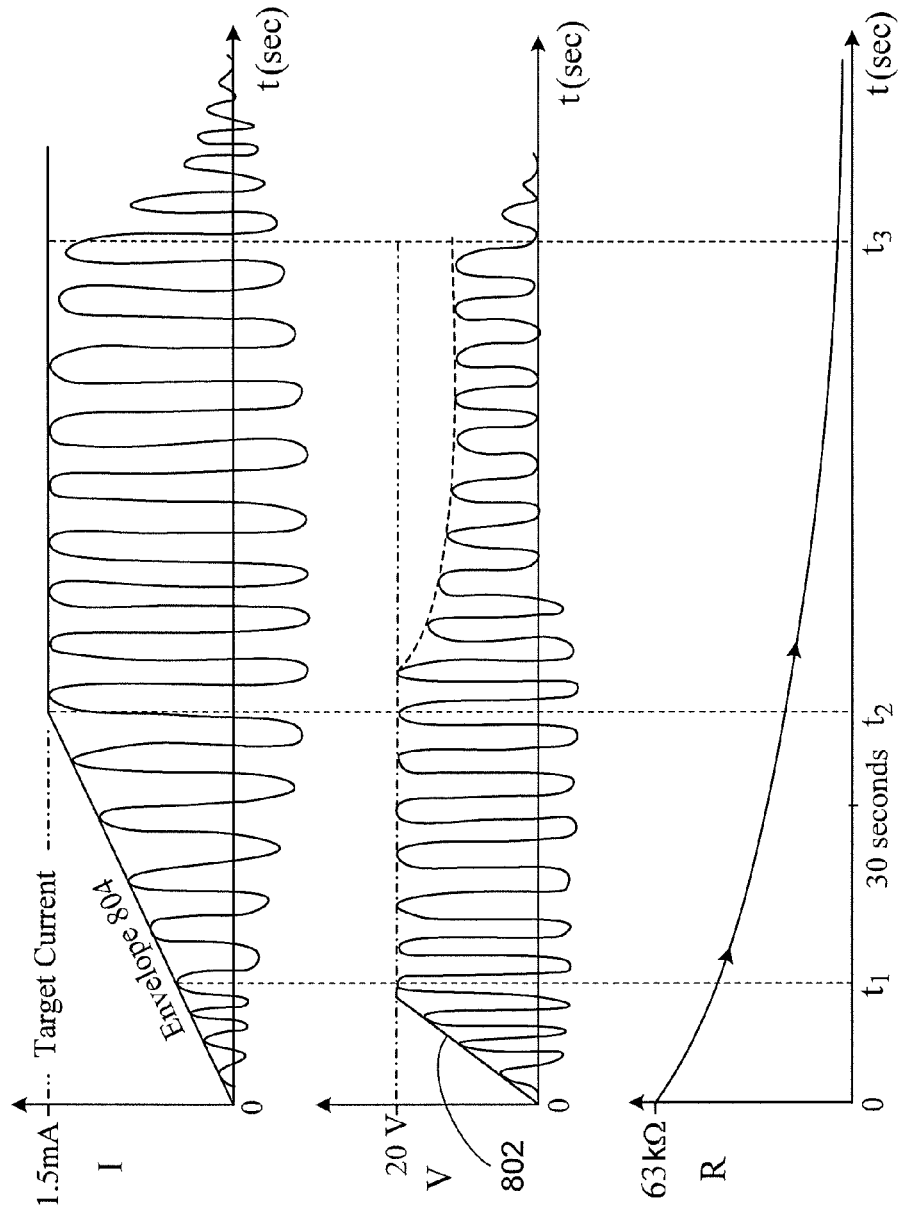
FIG. 8 includes three graphs showing how current, voltage and resistance, respectively, changes over time during an exemplary transcranial current stimulation procedure.

FIG. 8 shows an example of changes in electrical current flow ("I" in the top chart), voltage ("V" in the middle chart) and resistance ("R" in the bottom chart) that occur over time during an exemplary transcranial Alternating Current Stimulation procedure. In the illustrated charts, the electrical current flow, the voltage, and the resistance are represented by the vertical axes. Time ("t" in each chart) is represented by the horizontal axes in the charts. In the illustrated example, the target current has been set at 1.5 milliamps, the first predetermined limit on voltage has been set at 20 volts and the duration has been set at 10 minutes (i.e., 600 seconds).

In contrast with the example shown in FIG. 3 (and discussed above), the example shown in FIG. 8 involves the use of an alternating (e.g., A.C.) waveform for current and voltage.

According to the illustrated example, at time T0, the process is initiated. The A.C. voltage (V) across the electrodes beings to ramp-up so that its outer envelope 802 begins to increase from zero volts and the A.C. current correspondingly begins to ramp-up toward the target value of 1.5 milliamps. In the illustrated example, the target value of 1.5 milliamps is reached when an outer envelope, defined by the alternating waveform of the A.C. current reaches 1.5 milliamps. In the illustrated example, the initial external resistance is 63 kilo-ohms, which begins to drop essentially as soon as the electrical current begins to flow.

At time T1, the voltage (V) being produced by the tDCS device across the electrodes reaches the first predetermined voltage limit of 20 volts. Notably, this occurs before the current (I) reaches the target value of 1.5 milliamps.

Beginning at time T1, the tDCS device prevents the voltage across the electrodes from increasing beyond the first predetermined limit of 20 volts. Subsequently, the tDCS device maintains the voltage (V) across the electrodes within the predetermined voltage limit of 20 volts until time T2, which is 60 seconds in the illustrated example, when the current (I) reaches the target value of 1.5 milliamps. Between T1 and T2, the external resistance continues to drop and, therefore, the current continues to increase even though the voltage is maintained at a substantially constant level.

According to the illustrated implementation, the target current of 1.5 mA, peak, is substantially maintained for the set duration of 10 minutes (i.e., 600 seconds) from time T2 until time T3. During this period of time, from T2 to T3, the external electrical resistance continues to decrease in a substantially asymptotic manner. In order to maintain the flow of electrical current substantially constant, at or about the target value of 1.5 milliamps, the voltage is reduced in a manner that is proportionally tracks the changes in external electrical resistance during this time period.

After time T3, the voltage and current are ramped down to zero over a period of time, which, in the illustrated implementation, is about 30 seconds. The external electrical resistance during this period of time tends to increase a bit, as represented in the illustrated example.

A number of embodiments of the invention have been described. Nevertheless, it will be understood that various modifications may be made without departing from the spirit and scope of the invention.

For example, in some implementations, it may be desirable to "jump start" the resistance drop process by jumping very quickly from 0 mA to some current above 0 mM (e.g., above 0.5 mA, which would generally be below the patient's sensation threshold) and holding the current at that level for some period of time (e.g., approximately 20 seconds), and then ramping up toward the target current. In some instances, this technique may help "push" down the resistance faster.

Moreover, in some embodiments, the increase in voltage may be facilitated by very quickly jumping from 0 volts across the electrodes to a first voltage level (e.g. 5 V) and holding that first voltage level as the current increases. This could be done, for example, for some amount of time (e.g., the first 15 seconds of stimulation), after which point the tDCS device would move to a "current controlled" stimulation with the, perhaps a higher, voltage limit.

For example, any number of electrodes may be used to deliver tDCS. One or more may be placed off head, for example, on the patient's neck or shoulder. Moreover, the electrodes 104*a*, 104*b* may be coupled to the patient's head in a variety of ways including by virtue of an electrode cap (not shown) or by use of an adhesive material to hold the electrodes in place.

The techniques disclosed herein can be adopted to deliver a variety of different types of neurostimulation.

The order of steps described in connection with various methods and techniques disclosed herein can be varied. Indeed, in some implementations, certain steps may be omitted completely.

Some of the parameters discussed (e.g., the first predetermined voltage limit) may be factory set and not adjustable by an operator in the field.

A variety of mechanisms can be provided to enable the human operator to set the various parameters including, for example, buttons, switches, touchscreens, or the like. Certain controls used during the tDCS procedure can be automated or manually controlled. Additionally, the panel and various hardware and circuitry of the tDCS device can differ in a number of ways.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

Certain of the operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) that facilitates at least some of the techniques disclosed herein can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In some embodiments, multiple stimulation devices may be operated in serial or parallel where one or more of the current sources function as described. These multiple devices may be connected to each-other or the body using one or more known electrical switching mechanisms forming a circuit. The switches may be adjusted prior or during stimulation while maintaining the operating features disclosed above.

In some implementations, the electrodes or the entire device may be implanted. For the purpose of applying very low current, the device will generally still reduce the required voltage to 1 V or less. While for the purpose of applying high-current use, the device will reduce the total required voltage.

When the stimulation is supra-threshold and used to trigger an all-or-none response, such as action potential or seizures, the voltage limit may be adjusted based on the threshold for the response. When the stimulation is voltage controlled but the voltage provided is monitored, this approach may be used by regulating this voltage. In this case, additional current limiting or current control features may be implemented. The first voltage limit may adjusted based on application of subject specific features, such that for some subjects the first voltage limit may be lowered. This may be the case for children, elderly people and/or individuals with skull defects, strokes, neuropsychiatric illnesses or the like.

The first voltage limit may be a function of time or device performance. For example, the first voltage limit may decrease with time from the start of stimulation.

The waveform may be any repetitive, cyclic, or repeating waveform including sinusoidal, square, pulses, or trapezoidal waveform, where these waveforms are monophasic or biphasic. The waveform may be charge balanced. The waveform may also include noise components such as white noise or spikes. The waveform may be composed of a combination of the above. The waveform may be composed of independent components where all or a portion of the components is repeated over time. When the waveform is repeated over time, in such a wave that the current returns to zero or near zero for a substantial portion of time, typically greater than 10 seconds, then as the current is increased again, the voltage limit may be applied as described. The same or a new voltage limit may be applied. In one embodiment, the waveform is a monophasic square wave which is "on" for 5 minutes and "off" for 5 minutes, and during each on phase the current is increased to a target value but the voltage is maintained at a predetermined limit prior to the current reaching the target value.

The waveform may be composed of two or more sinusoids. In this case, the voltage limit may be applied to only of the sinusoids, to each of the sinusoids independently, or to the combination of both sinusoids as reflected in the combined waveform. For example, if the waveform applied includes two sinusoids, where the frequency of the first sinusoid is greater than 100 times the frequency of the second sinusoid, than the voltage limit may be applied only the amplitude of the first sinusoid and the total voltage applied may exceed the voltage of the combined sinusoids. In general, where the signal is composed of a lower and high frequency components, the voltage limit may be applied to only the low frequency components, only the high frequency components, or to the total signal.

The term resistance is used herein and should be construed broadly to include the concept of impedance as well. The resistance of the electrodes and body may be complex and frequency dependent such that impedance may be used to describe the relationship between voltage and current in a manner that does not deviate with the current disclosure. The voltage limit can be applied at one or more specific frequencies as described or using the peak (sum). Electrical impedance can indicate the ratio of the voltage phasor to the electric current phasor, a measure of the opposition to time-varying electric current in an electric circuit including the body. Prior or during stimulation, the impedance can be calculated by complex division of the voltage and current. The impedance can be calculated, for example, by applying a sinusoidal voltage to the device in series with a resistor, and measuring the voltage across the resistor and across the device. Performing this measurement by sweeping the frequencies of the applied signal provides the impedance phase and magnitude. The use of an impulse response may be used in combination with the fast Fourier transform (FFT) to rapidly measure the electrical impedance of various electrical devices. Other methodologies such as network and impedance analyzers while provide additional versatility in the electrical impedance measurement. The model of the system used in the controller may include representation of impedance.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method of delivering neurostimulation to a patient, the method comprising:
    setting a desired target value for electrical current and a target time duration for delivery of the target value of electrical current to the patient, said current target value and said target time duration defining a therapeutic neurostimulation potential delivered to the patient;
    measuring electrical resistance between a first electrode and a second electrode coupled to the patient;
    setting a first predetermined voltage limit to be applied across the first and second electrodes based at least in part on the measured electrical resistance, the first predetermined voltage limit having a voltage value different than the voltage required to reach the desired current target value based on the measured resistance;
    initiating a flow of electrical current through the first electrode and the second electrode coupled to the patient;
    increasing a voltage across the first and second electrodes to thereby control the rate of increase in the flow of electrical current toward the target value during a current-controlled ramp-up period;
    preventing the voltage across the first and second electrodes from increasing beyond the first predetermined limit prior to reaching the target current value during the ramp-up period; and
    controlling the voltage within the predetermined range during a voltage-controlled control mode for a period of time, wherein the amplitude of the electrical current continues to increase toward the target value during at least part of the time when the voltage across the first electrode and the second electrode is maintained at or near the voltage limit for a period of time,
    wherein the target time for duration of delivery of the target current is significantly greater than the period of time that the voltage is controlled within the predetermined range such that the therapeutic neurostimulation potential is not changed even as a maximum voltage is potentially decreased, and
    wherein the first predetermined voltage limit is selected in a range such that the target current value is reached.

2. The method of claim 1 further comprising:
    adjusting the voltage across the first electrode and the second electrode after the target current has been reached to substantially maintain the electrical current at the target value.

3. The method of claim 2 further comprising:
substantially maintaining the electrical current at the target value for a period of time sufficient to produce a therapeutic effect in the patient.

4. The method of claim 3 wherein the target value of current is between about 1 milliamp and about 3 milliamps, and wherein the period of time that the electrical current is substantially maintained at the target value is between about 10 minutes and 30 minutes.

5. The method of claim 3 further comprising:
delivering between about 600 millicoulombs and about 2400 millicoulombs of electric charge to the patient during the period of time that the electrical current is substantially maintained at the target value.

6. The method of claim 1 further comprising:
monitoring the flow of current, and
in response a determination that the monitored flow of current has not reached the target value within a predetermined amount of time, extending a period of time that the flow of current is to be delivered to the patient.

7. The method of claim 1 further comprising:
monitoring the flow of current, and
taking a responsive action to a determination that the monitored flow of current has not reached the target value within a predetermined amount of time,
wherein the responsive action is selected from the group consisting of alerting a human operator and extinguishing the flow of electrical current.

8. The method of claim 1 wherein the ramp-up period is between about 1 second and about 30 seconds.

9. The method of claim 8 wherein the ramp-up period is about 10 seconds.

10. The method of claim 8 wherein the flow of electrical current increases during the ramp-up period at an average rate of no more than about 1.5 milliamps per 30 seconds.

11. The method of claim 1 wherein the neurostimulation is transcranial direct current stimulation.

12. The method of claim 1 further comprising:
monitoring the voltage across the first electrode and the second electrode; and
disconnecting the voltage across the first electrode and the second electrode if the voltage across the first electrode and the second electrode exceeds a second predetermined limit indicating a circuitry malfunction,
wherein the predetermined second value is above the predetermined first value.

13. The method of claim 1 wherein the predetermined range is within about 10% of the first predetermined limit.

14. The method of claim 1 wherein increasing the flow of electrical current toward a target value comprises increasing the flow of electrical current monotonically.

15. The method of claim 1 wherein the voltage across the first and second electrodes is an alternating current.

16. The method of claim 1 further comprising:
applying a test stimulation to the patient;
monitoring a test voltage and a test current associated with the test stimulation;
generating a circuit model based on the monitored test voltage and test current;
using the circuit model to set one or more parameters associated with the electrical current and voltage in the delivery of neurostimulation to the patient.

17. The method of claim 1 further comprising:
increasing the voltage to a voltage level in a manner that accelerates a decrease in resistance across the electrodes.

18. The method of claim 1
wherein the amplitude of the electrical current continues to increase toward the target value during at least part of a time when the voltage across the first electrode and the second electrode is maintained within the predetermined range due to a decrease in electrical resistance from the initial electrical resistance between the first and second electrodes through the patient.

19. The method of claim 1, wherein, after the current achieves the target value, the voltage decreases below the first predetermined limit while the current is maintained at or near at the target value.

20. The method of claim 1, wherein the current does not decrease to zero or near zero from the time of initiating the current flow to the time the current reaches the target value.

* * * * *